(12) United States Patent
Merz et al.

(10) Patent No.: US 6,983,666 B2
(45) Date of Patent: Jan. 10, 2006

(54) ELECTRIC FURNACE BOTTOM PROBE

(75) Inventors: W. Allan Merz, Douglassville, PA (US); Wayne F. Egolf, Douglassville, PA (US)

(73) Assignee: CertainTeed Corporation, Valley Forge, PA (US)

( * ) Notice: Subject to any disclaimer, the term of this patent is extended or adjusted under 35 U.S.C. 154(b) by 54 days.

(21) Appl. No.: 10/717,661

(22) Filed: Nov. 21, 2003

(65) Prior Publication Data

US 2005/0109132 A1    May 26, 2005

(51) Int. Cl.
*G01B 7/28* (2006.01)
(52) U.S. Cl. .......................................... 73/866.5; 73/86
(58) Field of Classification Search .................... 73/86, 73/866.5, 863.81, 863.82, 863.83, 863.84; 374/139, 140; 266/99, 100
See application file for complete search history.

(56) References Cited

U.S. PATENT DOCUMENTS

| | | | | |
|---|---|---|---|---|
| 3,905,239 A | * | 9/1975 | Legille | 73/866.5 |
| 4,002,448 A | * | 1/1977 | Griffith et al. | 65/29.17 |
| 4,399,544 A | * | 8/1983 | Monaghan | 373/35 |
| 4,761,892 A | * | 8/1988 | Jankkila | 33/556 |
| 4,914,948 A | * | 4/1990 | Murakawa et al. | 73/290 R |

* cited by examiner

*Primary Examiner*—Robert Raevis
(74) *Attorney, Agent, or Firm*—Oblon, Spivak, McClelland, Maier & Neustadt, P.C.

(57) ABSTRACT

A furnace probe measuring system and method used to measure conditions, such as wear, within an electric furnace. A position assembly is configured to attach to a portion of an electric furnace. A probe assembly is moveably coupled to the position assembly and includes a location sensing portion configured to adjust to a location. A measurement device is coupled to the location sensing portion and indicates the location of the location sensing portion to determine wear.

51 Claims, 5 Drawing Sheets

ELECTRIC FURNACE BOTTOM PROBE

BACKGROUND OF THE INVENTION

1. Field of the Invention

The invention generally relates to a method and apparatus for electric furnace monitoring. More particularly, the invention relates to obtaining and evaluating furnace conditions.

2. Discussion of the Background

Operation of electric furnaces cause deterioration of the inside surfaces which include pavement of the furnace floor and electrode blocks. Determination of the conditions of the furnace floor or the electrode blocks during operation may be difficult when material, for example, molten material, within the electric furnace achieves high temperatures. Determination of the conditions of the electric furnace, however, is important to accurately schedule operation and maintenance, including rebuild, of the furnace. Measurement of wear within the furnace may be obtained by removing or draining the contents of the electric furnace.

The inventors of the present invention realized that quickly measuring the wear or deterioration within the electric furnace without removing the material would minimize negative effects on furnace stabilization and on production.

What is needed is an efficient method to measure wear within an electric furnace during operation.

SUMMARY OF THE INVENTION

Accordingly, the present invention advantageously provides a furnace probe positioning measuring system that includes a position assembly configured to attach to a portion of a furnace, a probe assembly movably coupled to the position assembly in which the probe assembly includes a location sensing portion configured to adjust to a location within the furnace, and a measurement device coupled so the location sensing portion in which the measurement device indicates the location of the location sensing portion.

The present invention further advantageously provides a method for measuring block erosion that includes the steps of inserting a position measuring probe into a furnace, obtaining a first position measurement and a second position measurement within said furnace, and comparing the first position measurement and the second position measurement to determine a difference between the first position measurement and the second position measurement. The difference is indicative of erosion associated with an electrode block.

Additional objects and advantages of the invention will be set forth in the description which follows, and in part will be evidence from the description, or may be learned by practice of the invention. The objects and advantages of the invention may be realized and obtained by means of the instrumentalities and combinations particularly pointed out hereinafter or by other instrumentalities and combinations.

BRIEF DESCRIPTION OF THE DRAWINGS

The accompanying drawings, which are incorporated in and constant to a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Embodiments of the present invention will be described hereinafter with reference to the accompanying drawings. In the following description, the elements that have substantially the same functions and arrangements are denoted by the same reference numerals, and repetitive descriptions will be made only when necessary.

Figure 1:
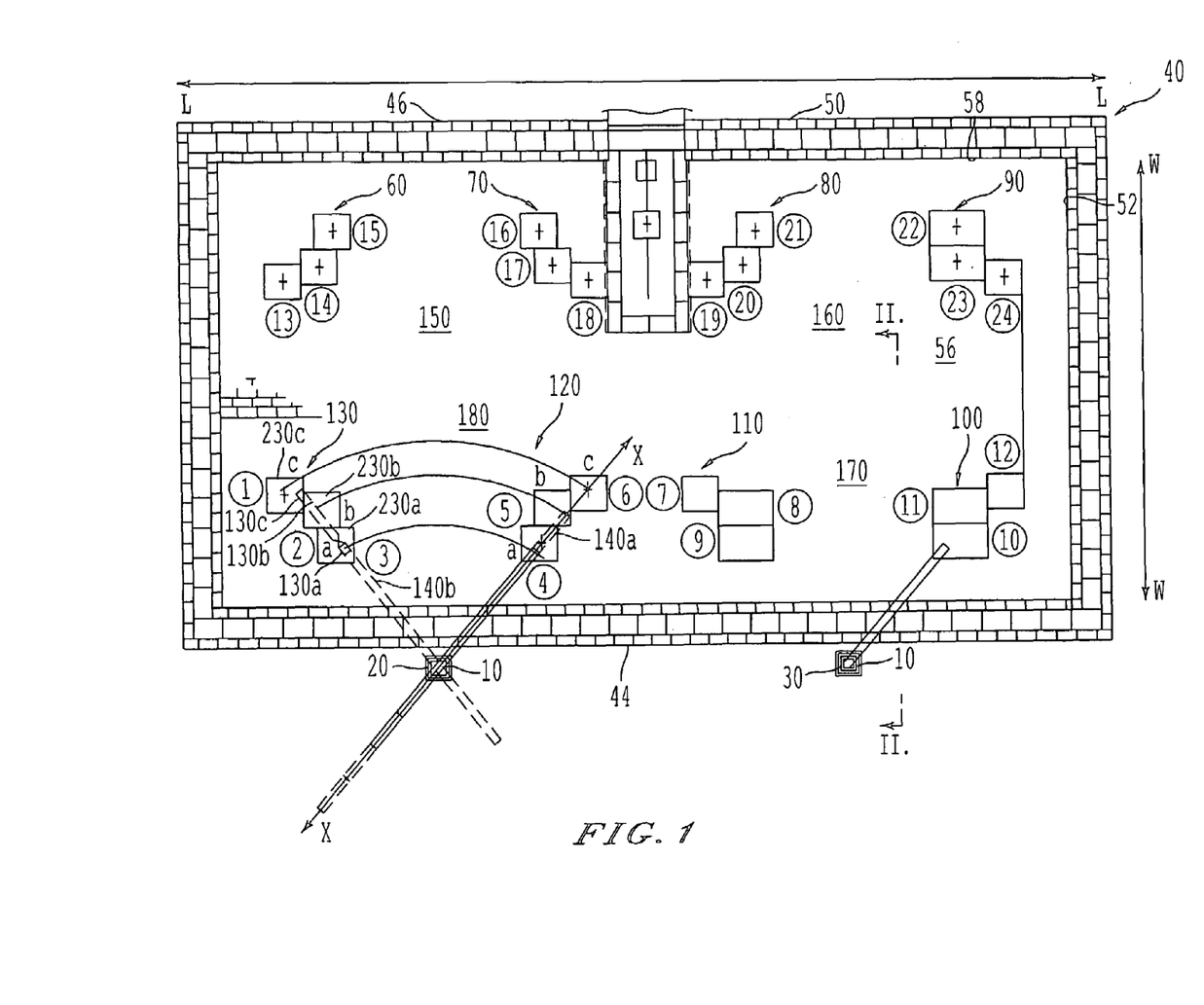
FIG. 1 is a plan view of an electric furnace with a probe assembly accordance with the present invention.
Figure 2:
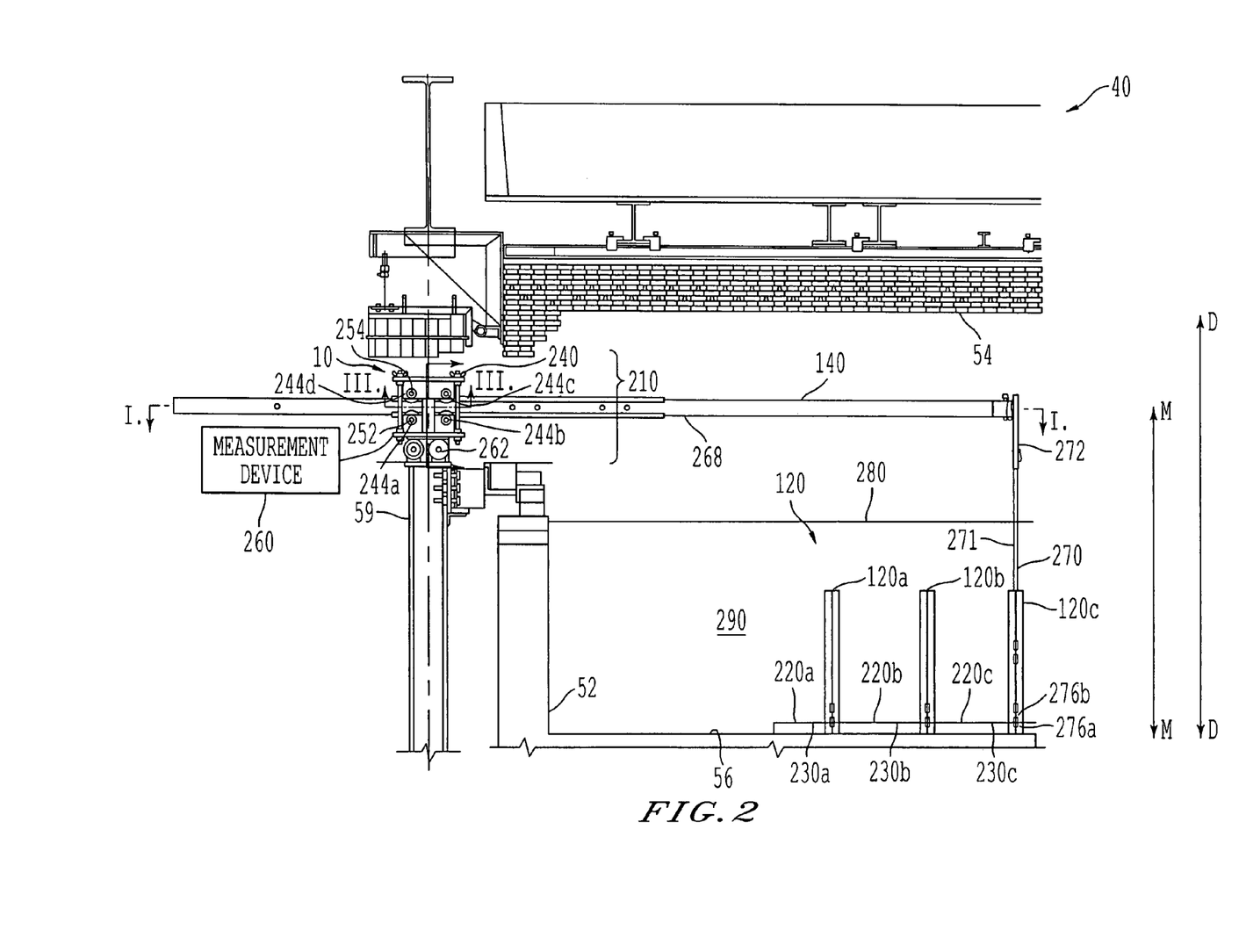
FIG. 2 is a sectional view of the electric furnace with the probe assembly taken along line II—II of FIG. 1.

Referring now to the drawings, wherein like reference numerals designate identical or corresponding parts throughout the several views, and more particularly to FIGS. 1 and 2, a furnace probe apparatus 10 is shown at a first set-up position 20. Alternatively, furnace probe apparatus 10 may be moved to a second set-up position 30 in an electric furnace 40. Each of first set-up position 20 and second set-up position 30 provides a location for measuring, for example, corrosion rate within the electric furnace 40. However, it should be appreciated that any type of appropriate measurements related to conditions within the electric furnace 40 or related to materials within a furnace may be taken, for example, temperature, humidity, and flow rate.

Electric furnace 40 includes a charging end 44 and a forehearth end 46. Electric furnace 40 also includes a furnace surface 52 for containing the material inside the electric furnace 40. Furnace surface 52 includes a furnace crown 54, a furnace bottom 56, and a perimeter wall 58 which retain molten material 280 or any other appropriate material which is heated or processed within electric furnace 40. Buckstays 59 are located outside of the perimeter wall 58 and are of a strength to support the furnace probe apparatus 10. The buckstays 59, for example, may be I-beams made of steel or other appropriate material.

In the alternate embodiment, the furnace probe apparatus 10 is positioned at the charging end 44; however it should be appreciated the furnace probe apparatus 10 may be at a position in which access to the desired location measurement may be obtained. For example, the furnace probe apparatus 10 may be positioned at the forehearth end 46 if "wear" and associated problems occur at this end.

Electric furnace 40 is a "bottom electrode" furnace in which electrodes are supported in the furnace bottom 56, alternatively the electric furnace 40 may be a "top electrode" furnace (not shown) in which electrodes are supported from outside the furnace perimeter wall 58 and are inserted through the top surface of the molten material 280. Bottom electrode furnaces may experience wear in the furnace bottom 56 and/or electrode blocks located within the furnace bottom. Top electrode furnaces also experience wear in the bottom surface.

In electric furnace 40, electrode banks 60, 70, 80, 90, 100, 110, 120 and 130 are disposed in the furnace bottom 56 as pairs in substantially identical configurations within electrode quadrant 150, 160, 170 and 180. Each electrode bank 60, 70, 80, 90, 100, 110, 120 and 130 includes electrodes and electrode blocks. For example, electrode bank 120 includes electrodes 120a, 120b, and 120c, and electrode bank 130 includes electrodes 130a, 130b and 130c. Although three electrodes are shown in the exemplary electrode banks, any number of electrodes may be provided depending on the configuration of the electric furnace 40. The electrodes 120a, 120b, 120c and 130a, 130b and 130c are positioned in a configuration within electric furnace 40 which is predetermined such that the positions of the electrodes may be known and may be referenced during a measurement process. Although only two electrode banks 120 and 130 have been described, it should be appreciated that the other electrode banks 60, 70, 80, 90 100 and 110 also may include electrodes positioned in a predetermined configuration.

Furnace probe apparatus 10 is located at first set-up position 20 at a distance proximate to electrode banks 120 and 130. The furnace probe apparatus 10 includes a translational member probe assembly 140 which extends outwardly to electrode bank 120 and is proximate to electrode 120a. However, it should be appreciated that the probe assembly may move within the electric furnace 40 to a variety of positions. For example, the dotted line portion 140a of the probe assembly 140 is an exemplary alternative extended position. Additionally, another exemplary position of the probe assembly 140 is shown as a dotted line portion 140b indicating the probe assembly 140 rotated to electrode bank 130 and proximate to electrode 130c. The probe assembly 140 is moved manually; however, it should be appreciated that automation of movement can also be implemented.

The repositioning of the probe assembly 140 may occur as a result of translational, articulational, and/or rotational movement. For example, with translational movement, the probe assembly 140 positioned to terminate proximate to electrode 120a, may move to any position along the axial pathway indicated by two-headed arrowed line x—x, and therefore be repositioned proximate to other electrodes 120b and 120c. However, it should be appreciated the probe assembly 140 may be extended a further distance than indicated by the two-headed arrowed line x—x depending on the length of the probe assembly 140. Additionally, for example, with articulational movement, the probe assembly 140 positioned to terminate at a location proximate to electrode 120a, may move to any position along the pathway indicated by arc a—a. Similarly, the probe assembly 140 positioned to terminate proximate to electrode 120b, may move to any position along the pathway indicated by arc b—b. Movement of the probe assembly 140 by translation and articulation provides displacement in two-dimensions, the length of the electric furnace 40, indicated by two-headed arrowed line L—L, and the width of the electric furnace 40, indicated by two-headed arrowed line W—W. It should be appreciated, however, that the probe assembly 140 may be moved in a third-dimension, the depth of the electric furnace 40, which is indicated by two-headed arrowed line D—D of FIG. 2.

Referring to FIG. 2, electric furnace 40 includes an exemplary electrode bank 120 supported within electrode blocks 220a, 220b and 220c, respectively. During the processing of the molten material 280 of the electric furnace 40, the electrode blocks 220a, 220b and 220c experience wear or deterioration at wear locations 230a, 230b and 230c, which are proximate to the electrodes 120a, 120b and 120c, respectively.

Furnace probe apparatus 10 includes a position assembly 240 and the probe assembly 140, and a measurement device 260. The probe assembly 140 is moveably supported by the position assembly 240.

Figure 3:
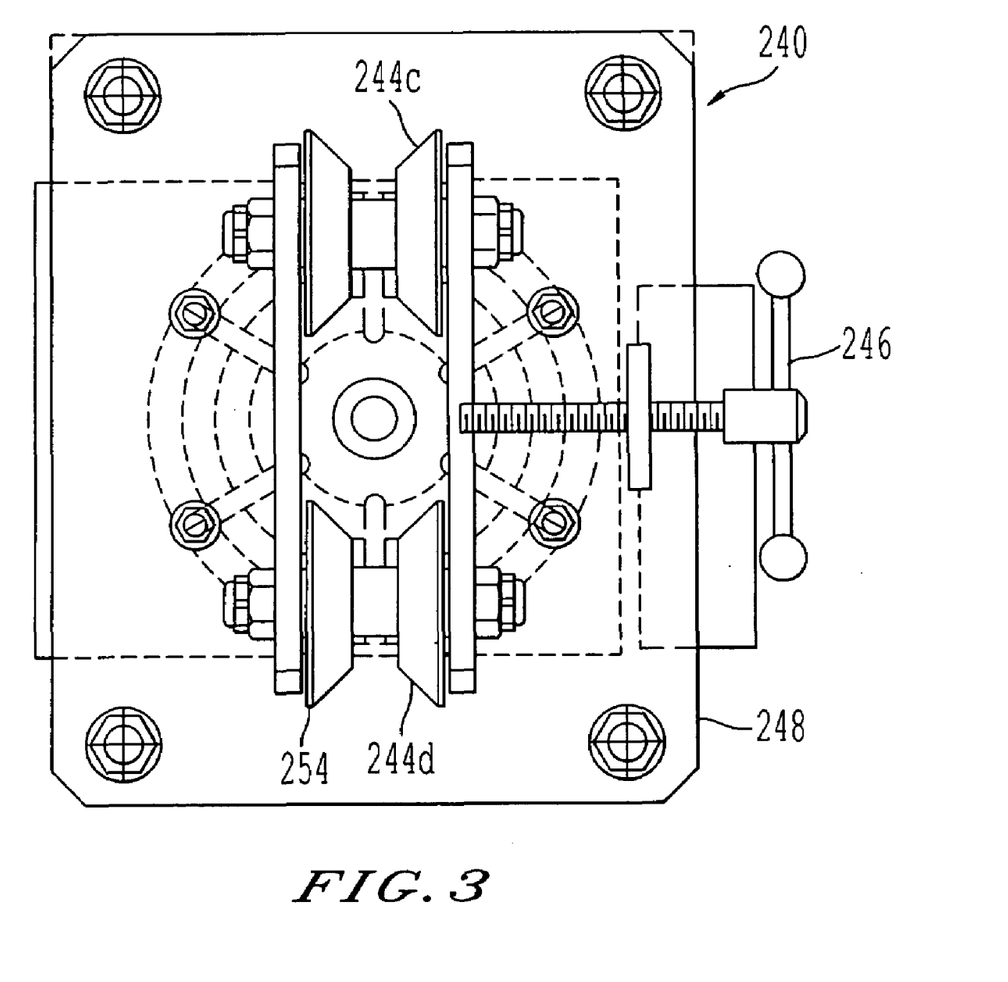
FIG. 3 is a sectional view of the positioning apparatus of the probe assembly taken along line III—III of FIG. 2.
Figure 4:
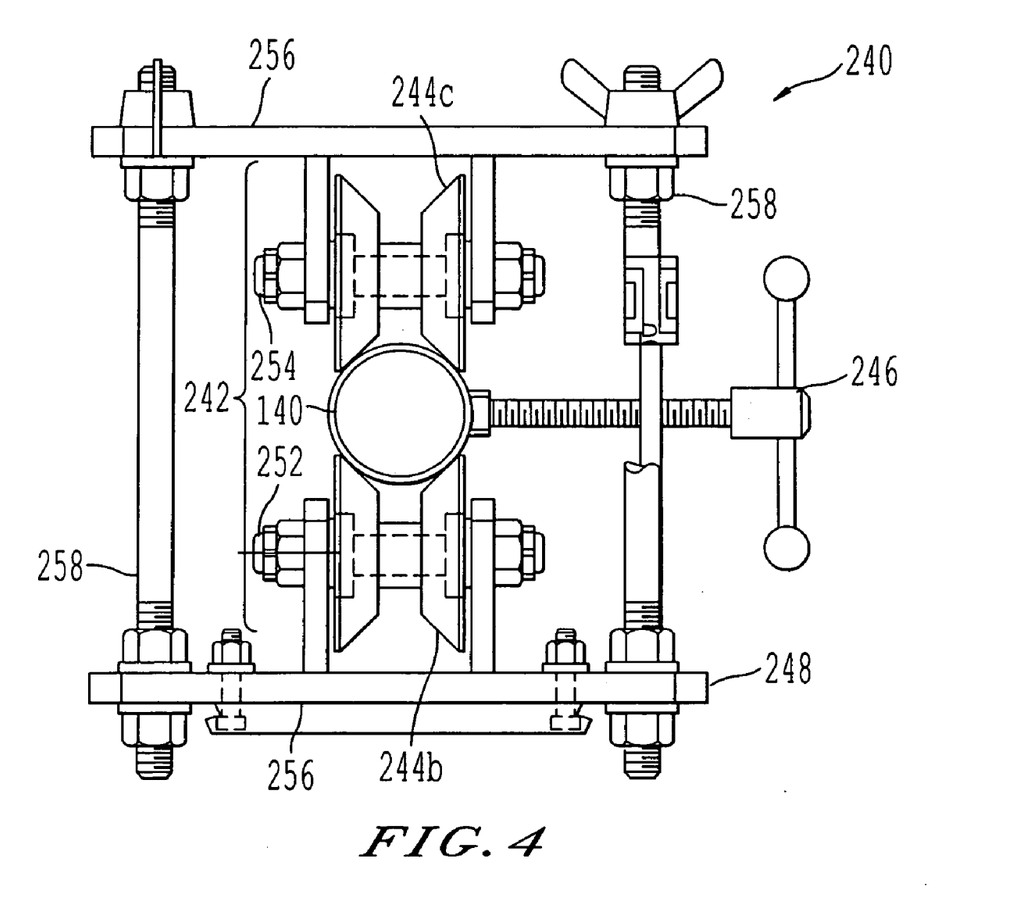
FIG. 4 is a sectional view of the positioning apparatus of the probe assembly taken along line IV—IV of FIG. 2.

Referring to FIGS. 2–4, the position assembly 240 includes a roller assembly 242 and a measurement device 260 or other appropriate measurement processing device which may store and process data related to measurements. Exemplary tables of data which may be obtained calculated and stored are provided in Tables 1–3. Roller assembly 242 includes 4 roller wheels 244a, 244b, 244c and 244d which are rotatably supported within roller assembly 242, a locking mechanism 246, and a housing 248. Roller wheels 244a and 244b form a lower roller assembly 252, which provide translational movement to probe assembly 140. Roller wheels 244c and 244d form an upper roller assembly 254 which also provides translational movement. In the alternate embodiment, roller wheels 244a, 244b, 244c and 244d are v-groove wheels; however, it should be appreciated that any appropriate device that can permit the probe assembly 140 to move in a translational direction may be used to support probe assembly 140. The locking mechanism 246 may secure the probe assembly at a location. Housing 248 includes a number of support members 256 joined together with nut and bolt assemblies 258. However, it should be appreciated that any appropriate housing construction may be used. The housing 248 may be attached to a tilting and/or rotating apparatus 262, for example a tilting/rotating table that allows movement of the positioning assembly 240 in at least one additional direction. In the alternate embodiment, two directions are permitted by the tilting rotating apparatus. The tilting rotating apparatus 262 may be coupled to buckstay 59 so that adequate support is given to the position assembly 240 and the connected probe assembly 140.

The probe assembly 140 includes a translating member 268 and a location sensing portion 270. The location sensing portion 270 is at least a length of the probe assembly 140 which is sufficient to be submerged within the depth of the molten material 290. For example, the location sensing portion length extends at least the magnitude of the distance from where the sensing portion 270 enters the top surface 280 of molten material 290 to where the wear locations 230a, 230b and 230c are positioned at the furnace bottom 56. The location sensing portion 270 may include an adjustable telescoping portion 271. The location sensing portion 270 may move from a low position 276a located proximate to furnace bottom 56 to a high position 276b located distal from the furnace bottom so that the location sensing portion 270 may measure wear, of various amounts, of the electrode blocks. In the exemplary embodiment, the location sensing portion 270 extends a length indicated by two-headed arrow line M—M and in a direction of about 90° from the axial direction of the probe assembly 140. Although the location sensing portion is a substantially linear shape, it should be appreciated that the location sensing portion 270 may be any appropriate alternate geometry, for example, a curved shape or an angled shape.

The location sensing portion 270 is made of a material that is resistant to deformation caused by high temperature thermal exposure generated, for example, by the molten material. For example, molten glass reaches high temperature up to about 2600° F. Stainless steel (Type 310) and molybdenum are two exemplary materials of which the sensing portion 270 may be made; however it should be appreciated that other materials which resist deformation at high temperature may be used. With low coefficients of thermal expansion, such thermally stable materials resist deformation and substantially maintain the initial predetermined geometry of the sensing portion 270.

Position measurements may be taken at a distance measured from the center line of each electrode, for example, at a distance of 6 inches. However, it should be appreciated that any appropriate distance may be used. Position measurements may be taken within the electric furnace for a duration of time in which the location sensing portion 270 maintains a substantially rigid and predetermined geometry. For example, a location sensing portion 270 that is extended into molten material, such as glass, may only remain submerged within the molten glass until the material of the location sensing portion begins to deteriorate, deform and/or break off into the molten material. One exemplary location sensing portion material, stainless steel (Type 310), remains rigid for one insertion into the molten glass for a duration of up to about 45 seconds. Another exemplary material, molybdenum, remains rigid for a duration of over 45 seconds, may be removed from the molten material for additional insertions, and thereby may be used through a number of heat-cool cycles before failure. The ability of the probe assembly 140 to rapidly obtain measurements minimizes negative effects on production and potential problems caused by deformed or broken location sensing portions.

Table 1 includes bottom probe readings for 12 position measurements at electrode designations 1–12 in FIG. 1. The position measurements or hot readings, which occur when the batch charging of the electric furnace and the power supplied to the electrodes is terminated and the molten material or heated conditions of the furnace is present, are for electrode designation of aluminu zirconia type material (AZS), "AZS w/3" SERV 30 CAP," "SERV 30" for different dates. Each electrode designation is provided with initial values, such as, but not limited to, appropriate probe depth settings of high or low which varies the vertical movement of the probe assembly 140, appropriate probe radii based on horizontal angle readings, vertical readings at the pavement, vertical readings at electrode and vertical angle readings. The pavement wear or electrode block wear may then be determined based on, for example, a vertical change in measured vertical angles and appropriate geometric calculations. For example, electrode wear at electrode 1, with a probe readings E is determined to have 2.5" of wear based on a difference of −1.08° in the vertical angle readings. The vertical angles are provided by measurement device 260, which is a commercially available "Digital Protractor." Using a microprocessor, it provides an immediate digital reading of all vertical angles in a 360° circle.

TABLE 1

| | | | | | | | | |
|---|---|---|---|---|---|---|---|---|
| BOTTOM PROBE READINGS | | | | | | | | |
| DATE | ELECTRODE DESIG-NATION | PROBE DEPTH SETTING | PROBE RADIUS | HORIZONTAL ANGLE READING (minutes) | VERTICAL∢ READING @ PAVERS (degrees) | VERTICAL ∢ READING @ ELECTRODE (degrees) | VERTICAL ANGLE READING Δ (degrees) | WEAR (inches) |
| 4/25 AM 2001 | 1 AZS | LOW | F | 39'–5' | | | | |
| | | | E | 41'–32' | 1.28° | 2.36° | −1.08° | 2½" |
| | 2 | LOW | D | 33'–50' | | | | |
| | | | C | 36'–42' | | | | |
| | 3 | LOW | B | 36'–31' | | | | |
| | | | A | 40'–2' | | | | |
| | 4 AZS w/3" SERVE 30 CAP | HIGH | A | 40'–2' | 3.69° | 1.7° | +1.99° | ¼" |
| | | | B | 36'–31' | | | | |
| | 5 | HIGH | C | 36'–42' | 2.99° | 2.99° | 0.00° | 3" |
| | | | D | 33'–50' | | | | |
| | 6 | HIGH | E | 41'–32' | 2.48° | 2.51° | −0.03° | 3" |
| | | | F | 39'–5' | | | | |
| | 7 AZS | LOW | F | 39'–5' | | | | |
| | | | E | 41'–32' | | | | |
| | 8 SERV 30 | LOW | D | 33'–50' | | | | |
| | | | C | 36'–42' | | | | |
| | 9 | LOW | B | 36'–31' | | | | |
| | | | A | 40'–2' | | | | |
| | 10 | LOW | A | 40'–2' | | | | |
| | | | B | 36'–31' | | | | |
| | 11 | LOW | C | 36'–42' | | | | |
| | | | D | 33'–50' | | | | |
| | 12 | LOW | E | 41'–32' | | | | |
| | | | F | 39'–5' | | | | |
| BOTTOM PROBE READINGS | | | | | | | | |
| DATE | ELECTRODE DESIG-NATION | PROBE DEPTH SETTING | PROBE RADIUS | HORIZONTAL ANGLE READING (minutes) | VERTICAL∢ READING @ PAVERS (degrees) | VERTICAL ∢ READING @ ELECTRODE (degrees) | VERTICAL ANGLE READING Δ (degrees) | WEAR (inches) |
| 4/25 PM 2001 | 1 AZS | LOW | F | 39'–5' | | | | |
| | | | E | 41'–32' | 0.79° | 2.17° | −1.38° | 3" |
| | 2 | LOW | D | 33'–50' | | | | |
| | | | C | 36'–42' | 1.01° | 2.37° | −1.36° | 2½" |
| | 3 | LOW | B | 36'–31' | | | | |
| | | | A | 40'–2' | 1.19° | 3.44° | −2.25° | 3½" |

FIELD MEASUREMENT

TABLE 1-continued

|   |   |   |   |   |   |   |   |   |   |
|---|---|---|---|---|---|---|---|---|---|
|   |   | 4 | AZS w/3″ SERVE 30 CAP | HIGH | A | 40′–2′ | 3.28° | 1.77° | +1.51° | ¾″ |
|   |   |   |   |   | B | 36′–31′ |   |   |   |   |
|   |   | 5 |   | HIGH | C | 36′–42′ | 2.71° | 1.49° | +1.22° | ¾″ |
|   |   |   |   |   | D | 33′–50′ |   |   |   |   |
|   |   | 6 |   | HIGH | E | 41′–32′ | 2.43° | 2.78° | −0.35° | 3¾″ |
|   |   |   |   |   | F | 39′–5′ |   |   |   |   |
| 4/26 AM 2001 | 7 | AZS | LOW | F | 39′–5′ | 1.32° | 2.51° | −1.19° | 2¾″ (1) |
|   |   |   |   |   | E | 41′–32′ |   |   |   |   |
|   |   | 8 | SERV 30 | LOW | D | 33′–50′ | 1.47° | 1.69° (1) | −0.22° | ½″ |
|   |   |   |   |   | C | 36′–42′ |   |   |   |   |
|   |   | 9 |   | LOW | B | 36′–31′ | 1.41° | 2.06° | −0.65° | 1″ |
|   |   |   |   |   | A | 40′–2′ | 1.34° | 1.98° | −0.35° | 1″ |
|   |   | 10 |   | LOW | A | 40′–2′ |   |   |   |   |
|   |   |   |   |   | B | 36′–31′ |   |   |   |   |
|   |   | 11 |   | LOW | C | 36′–42′ | 1.07° | 1.40° | −0.33° | ¾″ |
|   |   |   |   |   | D | 33′–50′ | 1.27° | 1.49° | −0.22° | ½″ |
|   |   | 12 |   | LOW | E | 41′–32′ | 1.12° | 1.22° | −0.10° | ¼″ |
|   |   |   |   |   | F | 39′–5′ |   |   |   |   |

Table 2 includes bottom probe readings from a cold check which occurs when the operation of the electric furnace is terminate and the furnace is emptied of molten material. For example, the measurement position, related to electrode 30 designation 7 with a probe radius of E, provided a confirmed hot reading of the corresponding field measurement, related to electrode designation 7, as indicated by a manual measurement.

Table 3 is an exemplary bottom probe reading conversion table for interpolation or determining the appropriate pavement wear or electrode wear based on geometric calculations as performed by Table 3. For each electrode designation, corresponding to an electrode block height relative to the bottom of the furnace, to a probe depth setting, to a probe radius, and to a horizontal angle reading, the table provides values representative of wear for various vertical angle

TABLE 2

BOTTOM PROBE READINGS

| DATE | ELECTRODE DESIGNATION | PROBE DEPTH SETTING | PROBE RADIUS | HORIZONTAL ANGLE READING (minutes) | VERTICAL∢ READING @ PAVERS (degrees) | VERTICAL∢ READING @ ELECTRODE (degrees) | VERTICAL ANGLE READING Δ (degrees) | WEAR (inches) |
|---|---|---|---|---|---|---|---|---|
| 5/4/2001 COLD CHECK | 1 | LOW | F | 39′-5′ |   |   |   |   |
|   |   |   | E | 41′-32′ |   |   |   |   |
|   | 2 | LOW | D | 33′-50′ |   |   |   |   |
|   |   |   | C | 36′-42′ |   |   |   |   |
|   | 3 | LOW | B | 36′-31′ |   |   |   |   |
|   |   |   | A | 40′-2′ |   |   |   |   |
|   | 4 | HIGH | A | 40′-2′ |   |   |   |   |
|   |   |   | B | 36′-31′ |   |   |   |   |
|   | 5 | HIGH | C | 36′-42′ |   |   |   |   |
|   |   |   | D | 33′-50′ |   |   |   |   |
|   | 6 | HIGH | E | 41′-32′ |   |   |   |   |
|   |   |   | F | 39′-5′ |   |   |   |   |
|   | 7 | LOW | F | 39′-5′ |   |   |   |   |
|   |   |   | E | 41′-32′ | 1.18° | 2.42° | −1.24° | 2¾″ (1) |
|   | 8 | LOW | D | 33′-50′ |   |   |   |   |
|   |   |   | C | 36′-42′ |   |   |   |   |
|   | 9 | LOW | B | 36′-31′ |   |   |   |   |
|   |   |   | A | 40′-2′ |   |   |   |   |
|   | 10 | LOW | A | 40′-2′ |   |   |   |   |
|   |   |   | B | 36′-31′ |   |   |   |   |
|   | 11 | LOW | C | 36′-42′ |   |   |   |   |
|   |   |   | D | 33′-50′ |   |   |   |   |
|   | 12 | LOW | E | 41′-32′ |   |   |   |   |
|   |   |   | F | 39′-5′ |   |   |   |   |

NOTES:
(1) - COLD CHECK CONFIRMED HOT READINGS.

reading differences which may be used to determine wear, based on interpolation. For example, for electrode designation 1, with a probe radius of E, a horizontal angle reading 41'-32', and a vertical angle reading difference of −1.08', the electrode wear is determined to be approximately 2.5 inches.

over time. Determining pavement wear over time may be done in the bottom electrode furnace or the top electrode furnace.

Figure 5:
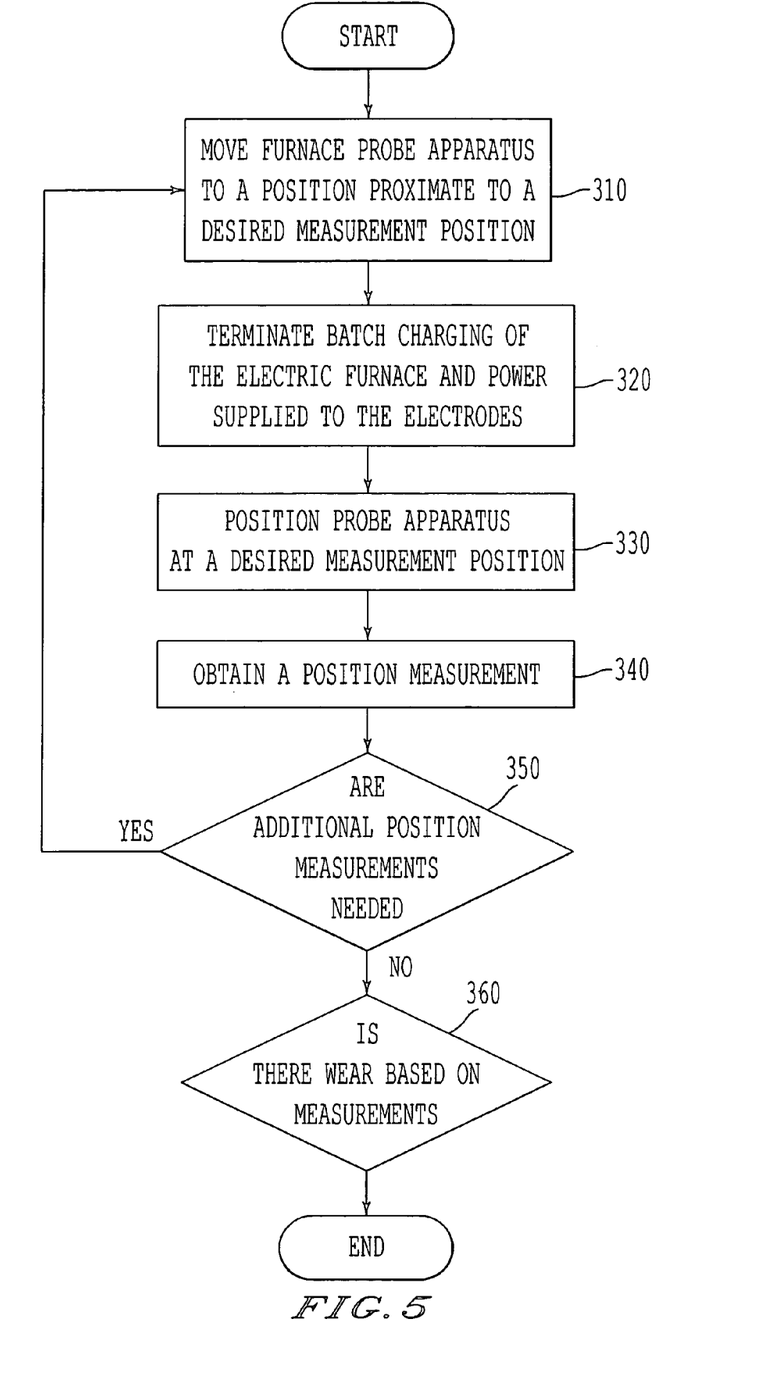
FIG. 5 is a block diagram illustrating a method of measuring position in the electric furnace of FIG. 1.

The present invention advantageously provides a method of measuring electrode block erosion. Referring to FIG. 5,

TABLE 3

BOTTOM PROBE READING CONVERSION TABLE

| PROBE SET-UP LOCATION | ELECTRODE DESIGNATION | ELECTRODE BLOCK HGT. | PROBE DEPTH SETTING | PROBE RADIUS | HORIZONTAL ANGLE READINGS | CONVERT Δ∢ TO Δh | | |
|---|---|---|---|---|---|---|---|---|
| | | | | | | Δh = ½" | Δh = 1" | Δh = 1½" |
| 1 | 1 | 0" | LOW | F | 39'-5' | −0.21' | −0.41' | −0.63' |
| | | | | E | 41'-32' | −0.21' | −0.43' | −0.66' |
| | 2 | 0" | LOW | D | 33'-50' | −0.25' | −0.50' | −0.73' |
| | | | | C | 36'-42' | −0.26' | −0.51' | −0.78' |
| | 3 | 0" | LOW | B | 36'-31' | −0.30' | −0.61' | −0.91' |
| | | | | A | 40'-2' | −0.33' | −0.65' | −0.98' |
| | 4 | 3" | HIGH | A | 40'-2' | +1.65' | +1.31' | +1.00' |
| | | | | 8 | 36'-31' | +1.53' | +1.23' | +0.93' |
| | 5 | 3" | HIGH | C | 36'-42' | +1.30' | +1.05' | +0.78' |
| | | | | D | 33'-50' | +1.23' | +1.00' | +0.75' |
| | 6 | 3" | HIGH | E | 41'-32' | +1.11' | +0.88' | +0.66' |
| | | | | F | 39'-5' | +1.05' | +0.85' | +0.96' |
| 2 | 7 | 0" | LOW | F | 39'-5' | −0.21' | −0.41' | −0.63' |
| | | | | E | 41'-32' | −0.21' | −0.43' | −0.66' |
| | 8 | 0" | LOW | D | 33'-50' | −0.25' | −0.50' | −0.73' |
| | | | | C | 36'-42' | −0.26' | −0.51' | −0.78' |
| | 9 | 0" | LOW | B | 36'-31' | −0.30' | −0.61' | −0.91' |
| | | | | A | 40'-2' | −0.33' | −0.65' | −0.98' |
| | 10 | 0" | LOW | A | 40'-2' | −0.33' | −0.65' | −0.98' |
| | | | | B | 36'-31' | −0.30' | −0.61' | −0.91' |
| | 11 | 0" | LOW | C | 36'-42' | −0.26' | −0.51' | −0.78' |
| | | | | D | 33'-50' | −0.25' | −0.50' | −0.73' |
| | 12 | 0" | LOW | E | 41'-32' | −0.21' | −0.43' | −0.66' |
| | | | | F | 39'-5' | −0.21' | −0.41' | −0.63' |

| PROBE SET-UP LOCATION | CONVERT Δ[ ]TO Δh | | | | | | | | |
|---|---|---|---|---|---|---|---|---|---|
| | Δh = 2" | Δh = 2½" | Δh = 3" | Δh = 3½" | Δh = 4" | Δh = 4½" | Δh = 5" | Δh = 5½" | Δh = 6" |
| 1 | −0.83' | −1.05' | −1.26' | −1.46' | −1.68' | −1.90' | −2.11' | −2.31' | −2.53' |
| | −0.88' | −1.11' | −1.31' | −1.55' | −1.78' | −1.98' | −2.21' | −2.43' | −2.66' |
| | −0.98' | −1.23' | −1.48' | −1.73' | −1.98' | −2.23' | −2.48' | −2.73' | −3.00' |
| | −1.05' | −1.30' | −1.56' | −1.83' | −2.11' | −2.36' | −2.63' | −2.90' | −3.16' |
| | −1.23' | −1.53' | −1.85' | −2.15' | −2.46' | −2.78' | −3.11' | −3.41' | −2.73' |
| | −1.31' | −1.65' | −1.98' | −2.31' | −2.65' | −2.98' | −3.33' | −3.66' | −4.01' |
| | +0.66' | +0.33' | 1.00' | −0.33' | −0.66' | −1.00' | −1.35' | −1.68' | −2.03' |
| | +0.61' | +0.31' | 1.00' | −0.31' | −0.61' | −0.93' | −1.25' | −1.56' | −1.88' |
| | +0.53' | +0.26' | 1.00' | −0.26' | −0.53' | −0.80' | −1.06' | −1.33' | −1.60' |
| | +0.50' | +0.25' | 1.00' | −0.25' | −0.50' | −0.75' | −1.00' | −1.25' | −1.50' |
| | +0.45' | +0.21' | 1.00' | −0.21' | −0.45' | −0.66' | −0.88' | −1.11' | −1.33' |
| | +0.41' | +0.21' | 1.00' | −0.21' | −0.41' | −0.63' | −0.85' | −1.06' | −1.28' |
| 2 | −0.83' | −1.05' | −1.26' | −1.46' | −1.68' | −1.90' | −2.11' | −2.31' | −2.53' |
| | −0.88' | −1.11' | −1.31' | −1.55' | −1.78' | −1.98' | −2.21' | −2.43' | −2.66' |
| | −0.98' | −1.23' | −1.48' | −1.73' | −1.98' | −2.23' | −2.48' | −2.73' | −3.00' |
| | −1.05' | −1.30' | −1.56' | −1.83' | −2.11' | −2.36' | −2.63' | −2.90' | −3.16' |
| | −1.23' | −1.53' | −1.85' | −2.15' | −2.46' | −2.78' | −3.11' | −3.41' | −3.73' |
| | −1.31' | −1.65' | −1.98' | −2.31' | −2.65' | −2.98' | −3.33' | −3.66' | −4.01' |
| | −1.31' | −1.65' | −1.98' | −2.31' | −2.65' | −2.98' | −3.33' | −3.66' | −4.01' |
| | −1.23' | −1.53' | −1.85' | −2.15' | −2.46' | −2.78' | −3.11' | −3.41' | −3.73' |
| | −1.05' | −1.30' | −1.56' | −1.83' | −2.11' | −2.36' | −2.63' | −2.90' | −3.16' |
| | −0.98' | −1.23' | −1.48' | −1.73' | −1.98' | −2.23' | −2.48' | −2.73' | −3.00' |
| | −0.88' | −1.11' | −1.31' | −1.55' | −1.78' | −1.98' | −2.21' | −2.43' | −2.66' |
| | −0.83' | −1.05' | −1.26' | −1.46' | −1.68' | −1.90' | −2.11' | −2.31' | −2.53' |

During measurement operation, the probe assembly 140 may be used to determine the differential wear between the paving at the furnace bottom 56 and each of the electrode blocks 220a, 220b and 220c by movement from one location to another such that a position measurement may be taken at each location. Alternatively, the probe assembly may be used to determine pavement wear, at a particular position, start block begins the "probing" or obtaining a measurement(s) at block 310 which moves the furnace probe apparatus 10 to a first location in the electric furnace 40, proximate to a where a measurement position is desired. For example, at a position near the electrode in which a determination of wear is desired, but not submerged within the molten material. To obtain the first position, the probe assembly 140 may be inserted quickly into the electric furnace 40 via the charging door 210. Within the electric furnace 40, the probe assembly 140 may move in three-dimensions. For example, the probe assembly 140 may move transversely, extending into the electric furnace 40 at varying lengths such that the probe assembly may be directed to any position along the width of the furnace indicated by two-headed arrowed line W—W. The probe assembly 140 also may rotate in a horizontal direction, by a tilting and/or rotating apparatus 262, such that the probe assembly 140 may be directed to any transverse position along the length of the furnace indicated by two-headed arrowed line L—L.

The horizontal position may be determined using a horizontal angle scale (not shown), which may include electronic sensors or mechanical sensing devices, or any other appropriate device which measures displacement from a horizontal reference position. Consequently, the movement in these directions locates the probe assembly 140 at the first position or nearer to the electrode in which a determination of wear is desired. The movement may occur outside of the molten material 290 or if the probe assembly is made of a material which is resistant to the high temperature of the molten material 290 and the batch charging conditions of the electric furnace, then movement may occur within the molten material 290.

The exemplary desired measurement position is located within a high temperature, electrically charged region of the electric furnace 40 where molten material 290 is present. Therefore, block 320 terminates the batch charging of the electric furnace and power supplied to the electrodes. This termination allows the probe assembly 140 to reposition within the molten material 290, and therefore at the measurement position.

Block 330 positions the probe assembly 140 at the measurement position, for example, an "electrode block wear position" which is at an electrode block a distance from the electrode or a "wear location" which is on the furnace crown 54 or furnace bottom 56. The probe assembly 140 may rotate in a vertical direction, by a tilting and/or rotating apparatus 262, such that the probe assembly may be directed to any position along the depth of the furnace indicated by two-headed arrowed line D—D. The vertical position may be determined by using a vertical angle scale (not shown). When, the probe assembly 140 moves and permits the location sensing portion 270 to be placed at the desired measurement position, the electrode block wear position measurement or wear location measurement is obtained. Block 340 obtains a position measurement based on geometric calculations via a measurement device 260. Determination block 350 determines if an additional position measurement is needed. An additional measurement is needed, for example, when determining wear of the electrode blocks. Not only may at least one electrode block wear position be obtained for each electrode block being assessed, but also a reference measurement may be needed. The measurement position of the electrode block may be compared to the additional measurement or "reference measurement," for example, of adjacent pavement relative to the electrode block. One exemplary reference measurement may be taken about 6 inches from the centerline of the electrode block. If an additional position measurement is needed, then block 310 iteratively moves the furnace probe assembly, after removal form the molten material, to a position proximate to the desired additional measurement position.

If an additional position measurement is not needed, then block 360 determines if the obtained position measurement is indicative of wear, for example, of either the electrode block or the furnace floor pavement the method ends. The first measurement may be compared to the reference measurement to determine the wear. For example, a position measurement of a substantially unworn electrode block, which is 5 inches in height from the pavement floor, should produce a desired position measurement indicative of about 5 inches greater than the reference measurement of the position of the pavement furnace floor. Alternatively, if the desired position measurement is of a current pavement floor which is compared to a reference measurement of the pavement floor taken before use, then the position measurement should be substantially equivalent to the reference position. If the position measurement is not equal to the reference measurement, then there is an indication of wear.

Using the positioning method as described above, the probe assembly 140 may be repositioned to yet additional measurement positions for electrode block measurements and pavement measurement positions at various locations within electric furnace 40.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

Obviously, numerous modifications and variations of the present invention are possible in light of the above teachings. It is therefore to be understood that within the scope of the appended claims, the invention may be practiced otherwise than as specifically described herein.

What is claimed is:

1. A furnace probe positioning measuring system, comprising:
   a positioning assembly configured to position proximate to a portion of a furnace;
   a probe assembly moveably coupled to said positioning assembly, said probe assembly including a translational member and a location sensing portion configured to adjust to a location of measurement within the furnace, said location sensing portion being provided on an end of said translational member, said location sensing portion having a telescoping portion with an adjustable length; and
   a measurement device coupled to said location sensing portion, said measurement device indicating the location of said location sensing portion.

2. The system of claim 1, wherein said translational member is coupled between said location sensing portion and said positioning assembly.

3. The system of claim 2, wherein said translational member and said sensing location portion are constrained to move together.

4. The system of claim 3, wherein said translational member provides displacement of said location sensing portion in a linear direction.

5. The system of claim 2, wherein said sensing location portion and said translational member are configured to form a substantially L-shape.

6. The system of claim 1, wherein said location sensing portion is a rigid member with a predetermined configuration.

7. The system of claim 1, wherein said location sensing portion is formed at least in part from a material having a coefficient of thermal expansion of at least a coefficient of thermal expansion of steel.

8. The system of claim 1, wherein said location sensing portion is formed at least in part from a material selected from the group consisting of steel, steel alloys and molybdenum.

9. The system of claim 1, wherein said positioning assembly further comprises:
a housing; and
a rotating/tilting member coupled to said housing such that said rotating/tilting member and said housing are constrained to move together by at least one movement of tilting and rotating.

10. The system of claim 9, wherein said rotating/tilting member is adapted to couple to the furnace.

11. The system of claim 9, wherein said rotating/tilting member is adapted to couple to a buckstay of the furnace or other rigid structure adjacent to the furnace.

12. The system of claim 1, wherein said positioning assembly further comprises:
a housing capable of supporting said probe assembly; and
at least one adjustment support moveably supporting said probe assembly in at least one direction, said probe assembly adjustably supported by said at least one adjustment support.

13. The system of claim 12, wherein said at least one adjustment support permits translational movement of said probe assembly, said at least one adjustment support being coupled to said housing.

14. The system of claim 12, wherein said at least one adjustment support includes at least a pair of v-groove wheels.

15. The system of claim 1, wherein said positioning assembly further comprises at least one stiffener configured to support said probe assembly and disposed against said probe assembly.

16. The system of claim 1, wherein said positioning assembly further comprises a probe lock capable of minimizing movement of said probe assembly.

17. A positioning measurement system, comprising:
a furnace;
a probe capable of being oriented at a position in a three-dimensional region, said probe including a translational member and a location sensing portion, said location sensing portion being provided on an end of said translational member, said location sensing portion having a telescoping portion with an adjustable length;
at least one positioning assembly configured to vary said position of said probe, said at least one positioning assembly coupled between said furnace and said probe; and
a measurement device in communication with said probe, said measurement device capable of determining a position of said location sensing portion in said three-dimensional region.

18. The system of claim 17, wherein said furnace further comprises:
a furnace surface;
at least one electrode configured to provide energy to said furnace;
an electrode block associated with said at least one electrode, said electrode block supported within said furnace surface, said at least one electrode supported in said electrode block; and
a wear surface formed on said electrode block proximate to said at least one electrode;
wherein said at least one adjustment member provides movement thereby adjusting the position of said probe to said wear surface.

19. The system of claim 17, wherein said furnace is one of a top electrode furnace and a bottom electrode furnace.

20. The apparatus of claim 17, wherein said translational member is coupled between said system location sensing portion and said positioning assembly, wherein said translational member provides linear displacement of said probe.

21. The system of claim 20, wherein said translational member and said sensing location portion are constrained to move together.

22. The system of claim 20, wherein said translational member provides displacement of said location sensing portion in a linear direction.

23. The system of claim 20, wherein said sensing location portion and said translational member are configured to form a substantially L-shape.

24. The system of claim 17, wherein said location sensing portion is a rigid member with a predetermined configuration.

25. The system of claim 17, wherein said location sensing portion is formed at least in part from a material having a thermal expansion coefficient of at least a steel thermal expansion coefficient.

26. The system of claim 17, wherein said location sensing portion is formed at least in part from a material selected from the group consisting of steel, steel alloys and molybdenum.

27. The system of claim 17, wherein said at least one positioning assembly further comprises:
a housing; and
a rotating/tilting member coupled to said housing such that said rotating/tilting member and said housing are constrained to move together by at least one movement of tilting and rotating.

28. The system of claim 27, wherein said rotating/tilting member is configured to couple to said furnace.

29. The system of claim 27, wherein said rotating/tilting member is configured to couple to a buckstay of said furnace or other rigid structure adjacent to the furnace.

30. The system of claim 17, wherein said at least one positioning assembly further comprises:
a housing capable of supporting said probe; and
at least one adjustment support moveably supporting said probe in at least one direction, said probe being adjustably supported by an at least one rotatable support.

31. The system of claim 30, wherein said at least one rotatable support is configured to permit translational movement of said probe, and said at least one rotatable support being coupled to said housing.

32. The system of claim 30, wherein said at least one rotatable support includes at least a pair of v-groove wheels.

33. The system of claim 17, wherein said at least one positioning assembly further comprises at least one stiffener configured to support said probe and disposed against said probe.

34. The system of claim 17, wherein said at least one positioning assembly further comprises a probe lock capable of minimizing movement of said probe.

35. The system of claim 17, wherein said at least one location sensing portion is interchangeable.

36. A furnace probe positioning measuring system, comprising:
- means for positioning proximate to a portion of a furnace;
- means for probing locations within furnace, said means for probing moveably coupled to said means for positioning and including a translational member and a location sensing portion configured to adjust to a location of measurement within the furnace, said location sensing portion being provided on an end of said translational member, said location sensing portion having a telescoping portion with an adjustable length; and
- means for measuring the location of measurement, said means for measuring coupled to said location sensing portion.

37. The system of claim 36, wherein said translational member is coupled between said location sensing portion and said means for positioning.

38. The system of claim 37, wherein said translational member and said location sensing portion are constrained to move together.

39. The system of claim 38, wherein said translational member provides displacement of said location sensing portion in a linear direction.

40. The system of claim 37, wherein said location sensing portion and said translational member are configured to form a substantially L-shape.

41. The system of claim 36, wherein said location sensing portion is a rigid member with a predetermined configuration.

42. The system of claim 36, wherein said location sensing portion is formed at least in part from a material having a coefficient of thermal expansion of at least a coefficient of thermal expansion of steel.

43. The system of claim 36, wherein said location sensing portion is formed at least in part from a material selected from the group consisting of steel, steel alloys and molybdenum.

44. The system of claim 36, wherein said means for positioning further comprises:
- a housing; and
- a rotating/tilting member coupled to said housing such that said rotating/tilting member and said housing are constrained to move together by at least one movement of tilting and rotating.

45. The system of claim 44, wherein said rotating/tilting member is adapted to couple to the furnace.

46. The system of claim 44, wherein said rotating/tilting member is adapted to couple to a buckstay of the furnace or other rigid structure adjacent to the furnace.

47. The system of claim 36, wherein said means for positioning further comprises:
- at least one adjustment support moveably supporting said means for probing in at least one direction.

48. The system of claim 47, wherein said at least one adjustment support permits translational movement of said means for probing, said at least one adjustment support being coupled to said housing.

49. The system of claim 47, wherein said at least one adjustment support includes at least a pair of v-groove wheels.

50. The system of claim 36, wherein said means for positioning further comprises at least one stiffener configured to support said probe assembly and disposed against said probe assembly.

51. The system of claim 36, wherein said means for positioning further comprises a probe lock capable of minimizing movement of said means for probing.

* * * * *